United States Patent [19]
Marko et al.

[11] Patent Number: 5,919,148
[45] Date of Patent: Jul. 6, 1999

[54] APPARATUS AND METHOD FOR EVALUATION OF SHOULDER STABILITY

[76] Inventors: Alexei J. Marko, 6-1976 West 3rd Avenue, Vancouver B.C., Canada, V6J 1L1; James A. McEwen, 10551 Bamberton Drive, Richmond, B.C., Canada, V7A 1K6; Brian Day, 4716 West 4th Avenue, Vancouver B.C., Canada, V6T 1C2; Michael Jameson, 2365 Badger Road, North Vancouver B.C., Canada, V7G 1S9; Septimiu E. Salcudean, 3936 W. 32nd Avenue, Vancouver B.C., Canada, V6S 1Z3; Peter D. Lawrence, 3511 West 26th Avenue, Vancouver B.C., Canada, V6S 1N6

[21] Appl. No.: 08/625,400

[22] Filed: Mar. 27, 1996

[51] Int. Cl.⁶ ....................................................... A61B 5/11
[52] U.S. Cl. .............................. 600/595; 600/546; 402/8; 601/33; 73/379.01
[58] Field of Search ..................................... 128/733, 774, 128/702; 601/33; 482/8, 9; 73/379.01; 600/546, 587, 595

[56] References Cited

U.S. PATENT DOCUMENTS

| 4,583,555 | 4/1986 | Malcom et al. . | |
|---|---|---|---|
| 4,649,934 | 3/1987 | Fraser et al. . | |
| 5,042,505 | 8/1991 | Mayer et al. . | |
| 5,275,174 | 1/1994 | Cook ....................................... | 128/774 |
| 5,335,674 | 8/1994 | Siegler . | |
| 5,391,132 | 2/1995 | Greenwald . | |
| 5,417,643 | 5/1995 | Taylor . | |
| 5,474,083 | 12/1995 | Chvech et al. ........................... | 128/733 |
| 5,513,651 | 5/1996 | Cusimano et al. ....................... | 128/782 |
| 5,520,181 | 5/1996 | Kreidler et al. ....................... | 128/653.5 |

FOREIGN PATENT DOCUMENTS

| 8804536 | 6/1988 | WIPO ..................................... | 128/774 |
|---|---|---|---|
| 9407414 | 4/1994 | WIPO ..................................... | 128/774 |

OTHER PUBLICATIONS

Komi et al. "A computerized Data Processing System for a Fatiove Experiment with a special Reference to EMG Activity" *Proceedings of the First National Meeting on Biophysics & Biotechnology*, Helsinki, Finland Jan. 4–5, 1973 pp. 211–213.

An Evaluation of the Shoulder Relocation Test, by Speer, et al. (Jul. 1992) reprinted in *American Journal of Sports Medicine*, 1994.

Classification and Physical Diagnosis of Instability of the Shoulder, by Silliman, et al. (Sep. 3, 1992) reprinted in *Clinical Orthopaedics and Related Research*, 1993.

*Primary Examiner*—John Mulcahy
*Attorney, Agent, or Firm*—ipsolon llp

[57] ABSTRACT

Apparatus for evaluating the stability of the shoulder joint of a human subject includes a rotatable, elbow-holding assembly that has sensors and associated processing components for producing an indication of the rotational angle of the long axis of the humerus of the subject relative to a reference. Sensors measure muscle activity as the humerus is rotated. Changes in the muscle activity measurement are processed to produce an indication of the changes in the subject's apprehension as the humerus is moved. The apparatus may include a clock that indicates the times when muscle activity occurs. The levels of muscle activity may be recorded at different times and indicated to the operator. Pressure can be applied in a direction normal to the long axis of the humerus, and sensors produce an indication of the level of the applied pressure and corresponding apprehension of the subject. Also available is an indication of the level of muscle activity that occurs when such pressure is applied.

4 Claims, 9 Drawing Sheets

APPARATUS AND METHOD FOR EVALUATION OF SHOULDER STABILITY

FIELD OF THE INVENTION

The invention is related to an apparatus for measuring parameters relating to the stability and function of the shoulder joint in the human body. More specifically, the invention relates to apparatus for quantitatively indicating the level of muscle activity associated with patient apprehension due to manipulation of the shoulder joint and for measuring the corresponding position and orientation of the shoulder joint.

BACKGROUND OF THE INVENTION

Many human subjects develop an unstable shoulder joint, usually as a result of injury, leading to symptoms which include pain, limited range of motion, and recurrent dislocation of the joint. For diagnostic purposes, and to assist in the assessment of the outcomes of various surgical interventions made in an effort to improve the stability of the joint, it is desirable to clinically evaluate the stability of the shoulder joint.

In the prior art, to clinically evaluate the stability of the shoulder joint, it has been common practice for the clinician to subjectively estimate the relative displacement of one bone of the joint (e.g. the humerus) with respect to another bone of the joint (e.g. the glenoid scapula) when a "relocation force" is applied near the head of the humerus toward the glenoid scapula, at specific positions and orientations of the joint. Also, many clinicians manipulate the humerus to note the range of motion possible in a symptomatic shoulder, and stop or limit these manipulations when the subject exhibits significant "apprehension", experiences pain, or actually experiences a dislocated shoulder joint. Contrary to clinical practice in the prior art, the inventors have discovered as a result of an initial clinical investigation that relative displacement of the humerus with respect to the glenoid scapula may not be consistently and significantly larger in a symptomatic shoulder than in a normal shoulder, and thus relative displacement may not be as clinically useful as previously thought in assessing shoulder joint stability for diagnostic purposes or to assist in the assessment of the outcomes of surgical interventions.

Also, in the prior art, clinical determination of the position and orientation of the bones forming the joint is subjective, imprecise and therefore difficult or impossible to reproduce for serial evaluations of changes in shoulder joint stability in the same subject. For example, in the prior art, clinicians have typically used a simple hand-held goniometer to estimate the orientation of the humerus relative to the torso of the subject. Also, in such prior-art determinations, the rate of change of the position and orientation of the humerus relative to the glenoid scapula, as well as the level of force applied near the head of the humerus, have been assessed only subjectively if at all by clinicians.

In the prior art, patient "apprehension" has been defined subjectively and clinical estimates of a patient's level of apprehension vary widely among even experienced clinicians. In the prior art, in determining the stability of the shoulder joint, the clinician may observe the apprehension exhibited by the patient as the humerus of the patient is manipulated through a desired range of motion relative to the glenoid scapula and force is applied near the head of the humerus. During those manipulations, apprehension is subjectively defined as the patient response to an oncoming feeling that the patient's shoulder joint is in a position of instability and may dislocate if the position and orientation of the bones comprising the joint is not changed to a stable position. Patient responses include a look or feeling of apprehension or alarm on the patient's face, resistance to further motion in the direction of instability, and verbally stating that this position duplicates the feeling of a previous dislocation. Thus in the prior art, an objective, quantitative indication of apprehension is not available to the clinician.

Finally, in the prior art, evaluation of changes in the stability of the shoulder joint over time, for use in patient outcome studies, has been dependent on the accuracy of a specific clinician's recorded subjective observations, and often on consistency in recorded observations among different clinicians. Furthermore, in the prior art it has not been common for any clinician to accurately measure or record the orientation of the arm during the test, thereby introducing a major variable and source of error into any serial comparisons.

SUMMARY OF THE INVENTION

The invention is directed to apparatus for improved assessment of the function of a shoulder joint of a human subject, comprising: angle transducing means for producing an indication of the rotational angle of the long axis of a humerus of a subject relative to a reference; muscle activity transducing means for producing an indication of the level of activity of a muscle of the subject; and apprehension indication means for producing an indication of a first level of muscle activity when the long axis is at a first rotational angle, for producing an indication of a second level of muscle activity when the long axis is at a second rotational angle, and for enabling an operator to compare the first level to the second level.

The apprehension indication means may include a reference level corresponding to the second rotational angle and may further produce an indication of the level of muscle activity relative to the reference level when the long axis is at the second rotational angle.

Advantageously, the apparatus includes a clock means for indicating the time at which the indication of the level of muscle activity is produced, and recording means for recording the level of muscle activity at a first time and for recording the level of muscle activity at a second time and for producing an indication for the operator of each of the levels at the first and second times respectively.

Force application means may also be included for applying a force to the long axis of the humerus and for producing an indication of the level of applied force, and the apprehension indication means may be further responsive to the force application means and may further produce an indication of the level of muscle activity when the force is applied.

BRIEF DESCRIPTION OF THE DRAWINGS

The invention will be better understood by an examination of the following description, together with the accompanying drawings, in which.

DETAILED DESCRIPTION OF THE PREFERRED EMBODIMENT

The embodiment illustrated is not intended to be exhaustive or limit the invention to the precise form disclosed. It is chosen and described in order to explain the principles of the invention and its application and practical use, and thereby enable others skilled in the art to utilize the invention. The preferred embodiment of the invention is described in three sections below: test description; hardware; and method of use.

Test Description

"Apprehension", as used with respect to the present invention only, shall be defined as the level of reflexive muscle activity resulting when one bone of a joint is moved by an externally applied force from a first position and orientation to a second position and orientation relative to a second bone of the joint, within a predefined time period.

The invention as described below is utilized to assess the stability of a patient's shoulder joint in the anterior direction i.e. in a direction normal to the frontal plane directed from the back surface of the body towards the belly surface of the body. Such an assessment is completed by performing in order an Apprehension Test, a Relocation Test and an Enhanced Apprehension Test. The Apprehension Test is undertaken by moving the arm of a patient from a first orientation, generally one in which the shoulder is stable, to a second orientation, generally one in which the shoulder is unstable and prone to dislocate, within a predefined time period. As the arm is moved from the first to the second orientation, the level of apprehension experienced by the patient is assessed. A positive Apprehension Test results when the patient is apprehensive at the second orientation. A negative Apprehension Test results when the patient is not apprehensive at the second orientation. The Relocation Test is then performed with the arm positioned at the second orientation by applying a posteriorly directed force to the head of the humerus. The application of posteriorly directed force to the head of the humerus increases the stability of the shoulder joint by preventing anterior dislocation of the humerus. A positive Relocation Test results when the application of the posteriorly directed force causes a reduction in the level of apprehension experienced by the patient. A negative Relocation Test results when either the patient is not apprehensive with their arm at the second orientation or the application of the posteriorly directed force does not reduce the level of apprehension experienced by the patient. The Enhanced Apprehension Test is then performed with the arm still positioned at the second orientation by applying an anteriorly directed force to the head of the humerus. The application of anteriorly directed force to the head of the humerus decreases the stability of the shoulder joint by assisting anterior dislocation of the humerus. A positive Enhanced Apprehension Test results when the application of the anteriorly directed force causes an increase in the level of apprehension experienced by the patient. A negative Enhanced Apprehension Test results when the application of the anteriorly directed force does not result in an increase in the level of apprehension experienced by the patient.

Hardware

Figure 1:
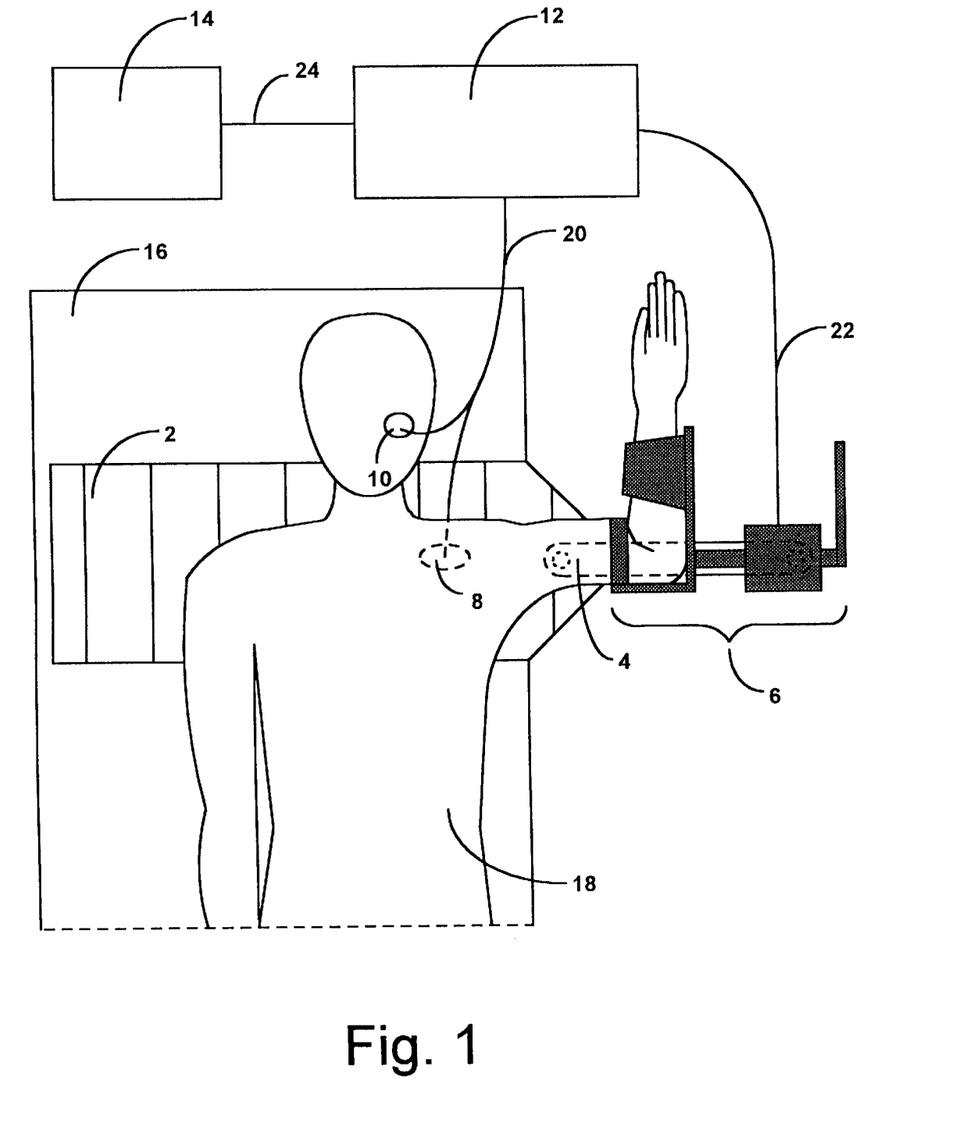
FIG. 1—is a simplified top view of the invention applied to the left arm of a patient.

Referring to FIG. 1 the invention comprises back support 2, extension arm 4, elbow constraint assembly 6, electrode pairs 8 and 10, processing unit 12 and printer 14. Back support 2 is shown resting upon examining table 16. A patient 18 is shown positioned upon back support 2 with the patients left elbow constrained within elbow constraint assembly 6, electrode pair 8 is shown applied to the left posterior shoulder region and electrode pair 10 is shown applied to the face of patient 18. Multi-conductor electrical cable 20 connects electrode pairs 8 and 10 to processing unit 12. Multi-conductor electrical cable 22 connects elbow constraint assembly 6 to processing unit 12. Multi-conductor electrical cable 24 connects processing unit 12 to printer 14.

Figure 2:
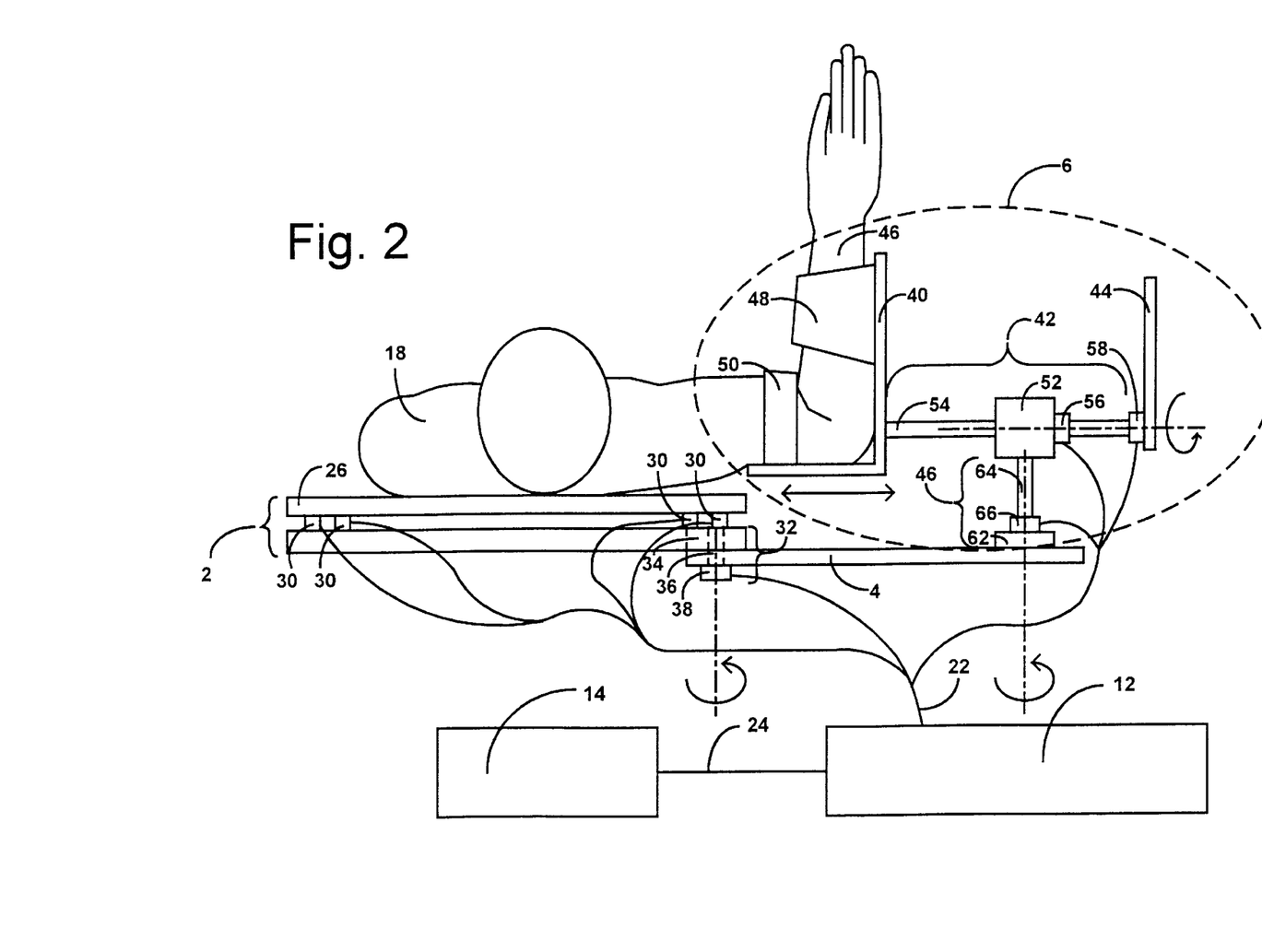
FIG. 2—is a detailed side view of the invention applied to the right arm of a patient.

Referring to FIG. 2 for a more detailed description of the apparatus, back support 2 comprises a top plate 26 on which the torso of patient 18 rests and a base plate 28 which rests against examining table 16. Top plate 26 is marked with grid-lines to assist an operator in orienting a patient 18 such that the torso of a patient 18 is at a known and clinically reproducible orientation relative to back support 2 to facilitate calculation of the abduction of the humerus in the frontal plane. Top plate 26 and bottom plate 28 of back support 2 are joined by four single axis force sensors 30 which are electrically connected to processing unit 12 by multi-conductor cable 22. As shown in FIG. 2, single axis force sensors 30 measure the components of force between top plate 26 and bottom plate 28 which are normal to the plane of back-support 2, and thereby provide a measure of any downward force applied to top plate 26 relative to examining table 16. Once patient 18 is positioned on back support 2, the summation of the forces measured by single axis force sensors 30 are indicative of the downward force on top plate 26 of back support 2 due to the weight of the torso of patient 18. Changes in the summation of the force measured by single axis force sensors 30 are indicative of the magnitude of changes in components of external forces normal to back support 2 which are applied to torso of patient 18. These external forces may include posteriorly directed pressure to the head of the humerus during Relocation Testing, as described above, which will cause an increase in the summation of the forces measured by single axis force sensors 30 or anteriorly directed forces applied during Enhanced Apprehension Testing, also described above which will result in a decrease in the summation of the forces measured by single axis force sensors 30.

While in the preferred embodiment the single axis force sensors have been described as oriented to measure forces normal to the plane of the top plate 26 it will be appreciated by those skilled in the art that the single axis force sensors 30 could be otherwise oriented to measure forces applied to the patient in other directions including a direction substantially normal to the long axis of the humerus or a direction along the long axis of the humerus.

As shown in FIG. 2, extension arm 4 is attached to bottom plate 28 of back support 2 by rotational bearing assembly 32. Rotational bearing assembly 32 comprises: bearing housing 34 which is fixed to bottom plate 28; bearing shaft 36 which is free to rotate within bearing housing 34; and rotational angle sensor 38 which produces a signal indicative of the angle of rotation of the central axis of bearing shaft 36 relative to the central axis of bearing housing 34. Extension arm 4 is attached to bearing shaft 36 thereby permitting extension arm 4 to rotate about the central axis of bearing housing 34 in a plane parallel to the plane of bottom plate 28 of back support 2 as indicated in FIG. 2. The signal produced by rotational angle sensor 38 is thereby also indicative of the angle of rotation of extension arm 4 relative to back support 2. Rotational angle sensor 38 is electrically connected to processing unit 12 by multi-conductor cable 22. Permitting extension arm 4 to rotate about the central axis of bearing housing 34 as indicated in FIG. 2 allows a patient's arm to be tested at different degrees of abduction in the frontal plane. Back support 2 can be reversed such that it can be used to test either the left or the right arm.

In the preferred embodiment, in order to minimize manufacturing costs, extension arm 4 is attached to back support 2 using the simple rotational bearing assembly 32 as described. At a greater cost to manufacture, the apparatus could be adapted to include a parallel linkage between bottom plate 28 and extension arm 4 which would allow extension arm 4 to be moved up or down in a direction normal to the plane of the back support 2. The configuration of a suitable parallel linkage is well established in the prior art. The inclusion of a parallel linkage would better facilitate the use of the invention on patients of different sizes, would allow the shoulder to be tested at different measures of anatomical extension of the humerus, and would allow the humerus to translate in the anterior and posterior directions when force is applied by the operator to the head of the humerus.

Elbow constraint assembly 6 fixed to the end of extension arm 4 is shown in detail in FIG. 2 and consists of: elbow support 40; rotational bearing assembly 42; handle 44; and rotational bearing assembly 46.

As shown in FIG. 2 the right arm of patient 18 is secured in elbow support 40 by two restraining straps 48 and 50. When a patients arm is properly secured by elbow support 40 the tibia and humerus of the arm are at a right angle, with the arm flexed 90 degrees at the elbow. Elbow support 40 is mounted on rotational bearing assembly 42 which comprises: bearing housing 52; bearing shaft 54 which is free to rotate within bearing housing 52; and rotational angle sensor 56 which produces a signal indicative of the angle of rotation of the bearing shaft 54 about its central axis relative to the central axis of bearing housing 52. Elbow support 40 is mounted to bearing shaft 54, such that an arm secured in elbow support 40 has the central axis of the humerus aligned with the central axis of bearing shaft 54. The signal produced by rotational angle sensor 56 is therefore also indicative of the angle of rotation of the humerus about its central axis relative to back support 2. Rotational bearing assembly 42 includes a handle 44 fixed to bearing shaft 54 through which the operator can apply rotational force to elbow support 40 to rotate humerus about the long axis as indicated in FIG. 2. Handle 44 includes torque sensor 58 which produces a signal indicative of the rotational force applied through handle 44 about the central axis of rotational bearing shaft 54 and thereby about the central axis of the humerus. Bearing shaft 54 is free to slide within bearing housing 52 as indicated in FIG. 2 thereby permitting the apparatus to adjust to differing humeral lengths.

As shown in FIG. 2 rotational bearing housing 52 is fixed to rotational bearing assembly 46 comprising: bearing housing 62; bearing shaft 64; and rotational angle sensor 66. Bearing shaft 64 is free to rotate within bearing housing 62; rotational angle sensor 66 produces a signal indicative of the angle of rotation of bearing shaft 64 about its axis relative to bearing housing 62. The signal produced by rotational angle sensor 66 is also indicative of the angle between the central axis of the humerus in the elbow support 40 and the central axis of the extension arm 4.

Rotational angle sensor 56, rotational angle sensor 66 and torque sensor 58 are electrically connected to processing unit 12 by multi-conductor electrical cable 22.

Figure 3:
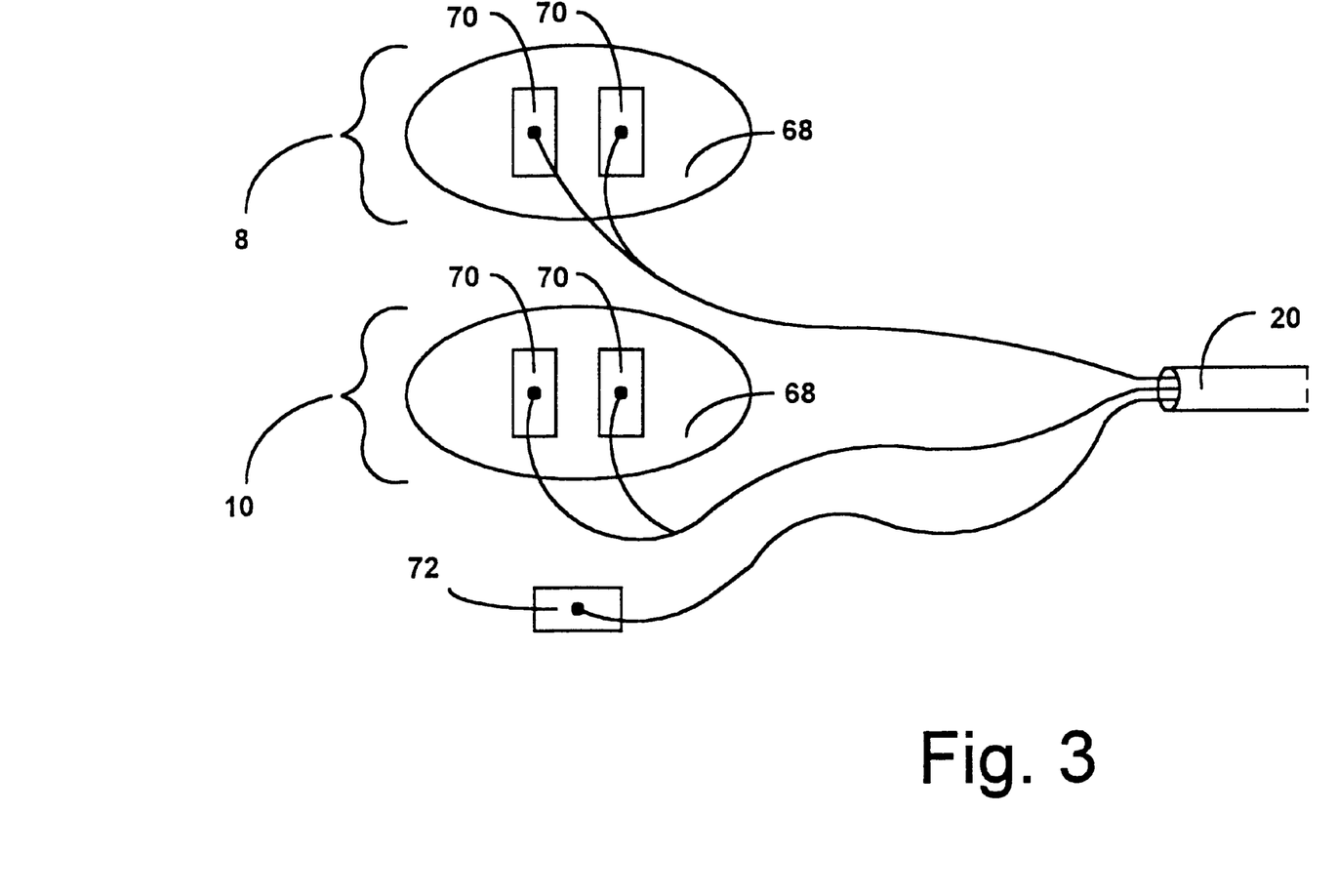
FIG. 3—is an illustration of the electrodes applied to a patient.

As shown in FIG. 3 electrode pairs 8 and 10 are mounted on flexible non-conductive adhesive backed sheets 68 such that the single electrodes 70 which comprise electrode pairs 8 and 10 are separated by a known distance. Electrode pair 8 is generally applied over superficial muscles of the shoulder being tested. Electrode pair 10 is applied over a muscle on the face of the patient to measure muscle activity during "frowning" of the patient which is associated with apprehension. Electrodes 70 are connected to the processing unit 12 (See FIG. 4.) by multi-conductor electrical cable 20. Single electrode 72, is also connected to processing unit 12 by multi-conductor electrical cable 20 and is applied elsewhere on the body of the patient to provide an electrical ground reference.

Processing unit 12 receives signals from rotational angle sensors 38, 56, 66, single axis force sensors 30, torque sensor 58 and electrode pair 8 and electrode pair 10 and analyzes these signals to determine orientation of the humerus, muscle activity, externally applied forces and thereby an indication of shoulder stability. Processing unit 12 receives input from an operator of the invention to control testing and generates reports for printing by printer 14. Details of processing unit 12 are shown in FIG. 4.

Figure 4:
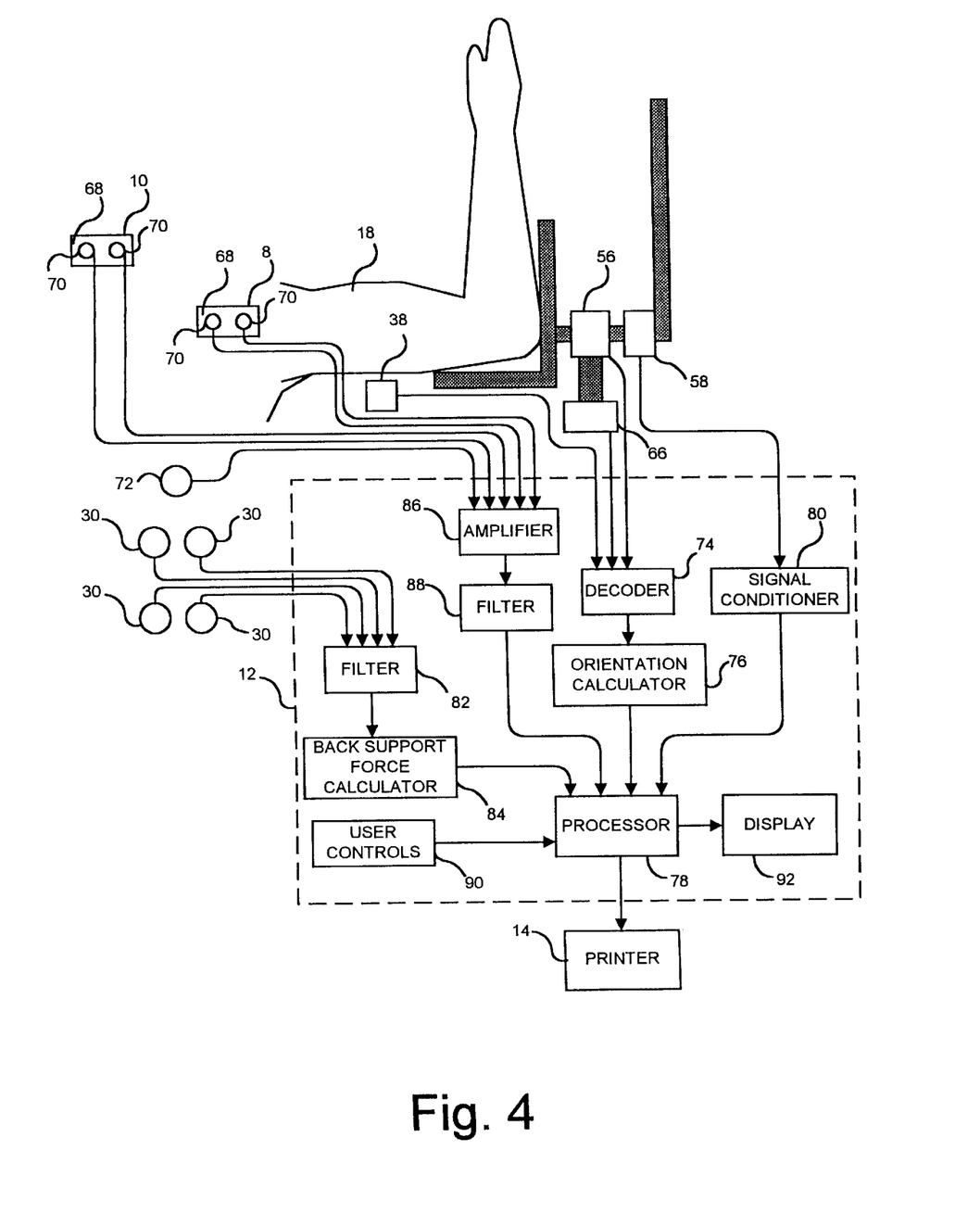
FIG. 4—is a block diagram illustrating the functions of the processing unit.

As shown in FIG. 4, the signal from rotational angle sensor 38 indicative of the angle of rotation of extension arm 4 relative to back support 2 is communicated to decoder 74. Also communicated to decoder 74 are: the signal from rotational angle sensor 56, indicative of the angle of rotation of the elbow support 40 about the central axis of bearing shaft 54 and thereby indicative of the angle of rotation of the humerus about its central axis relative to the back support 2; and the signal from rotational angle sensor 66, indicative of the angle of rotation of the rotational bearing assembly 42 about the central axis of bearing shaft 64 and thereby indicative of the angle between the central axis of the humerus in the elbow support 40 and the central axis of the extension arm 4. Decoder 74 acts to remove unwanted noise from the signals from the rotational angle sensors and converts the signals to a format suitable for communication to the orientation calculator 76.

Decoded signals from the rotational angle sensors 38, 56 and 66 are communicated to orientation calculator 76 which calculates the angle of abduction of the humerus in the frontal plane and the angle of rotation about the central axis of the humerus relative to back support 2.

Figure 5:
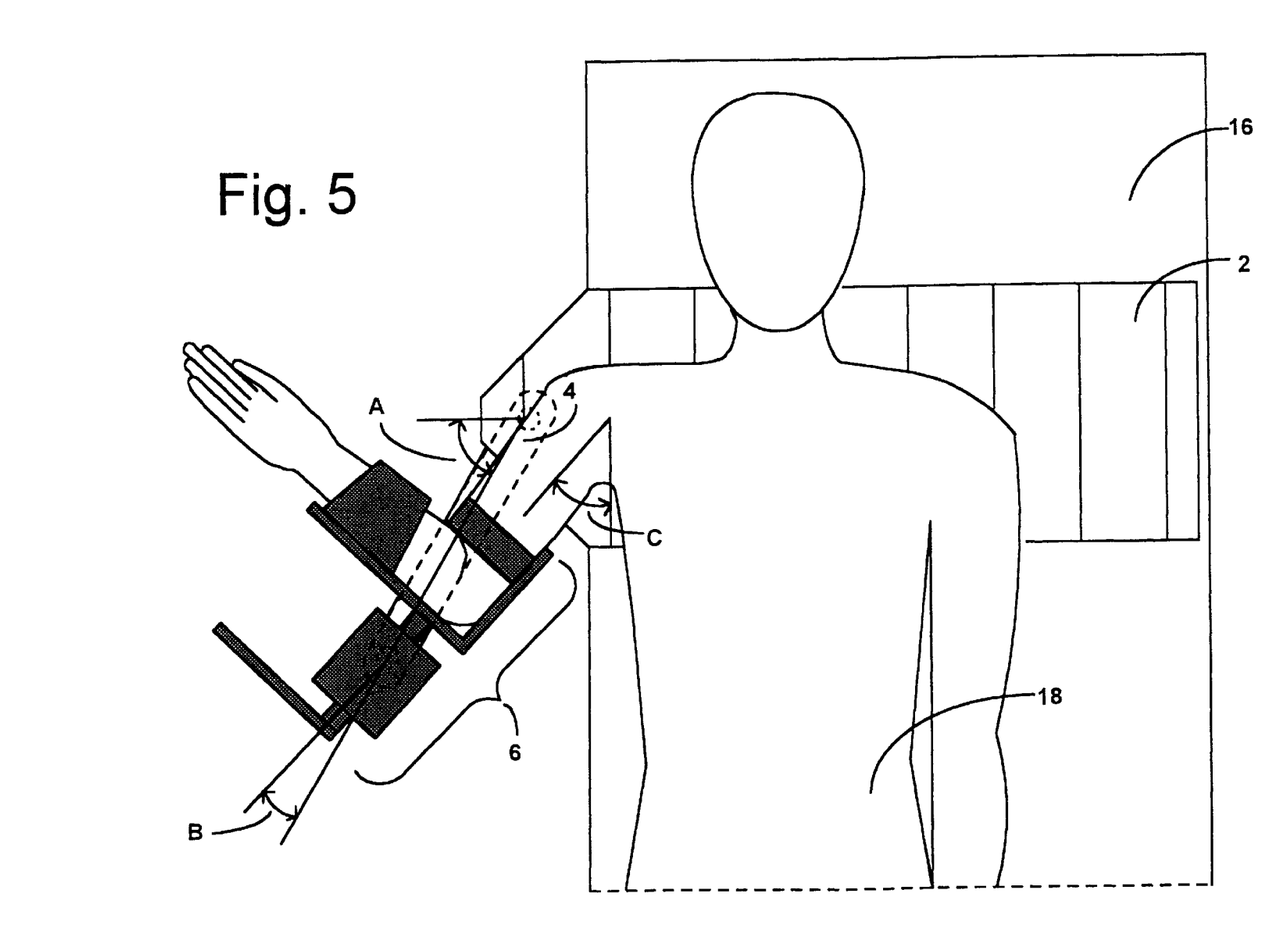
FIG. 5—shows the invention applied to the right arm of a patient and illustrates the method for calculating the abduction of the humerus in the frontal plane.
Figure 6:
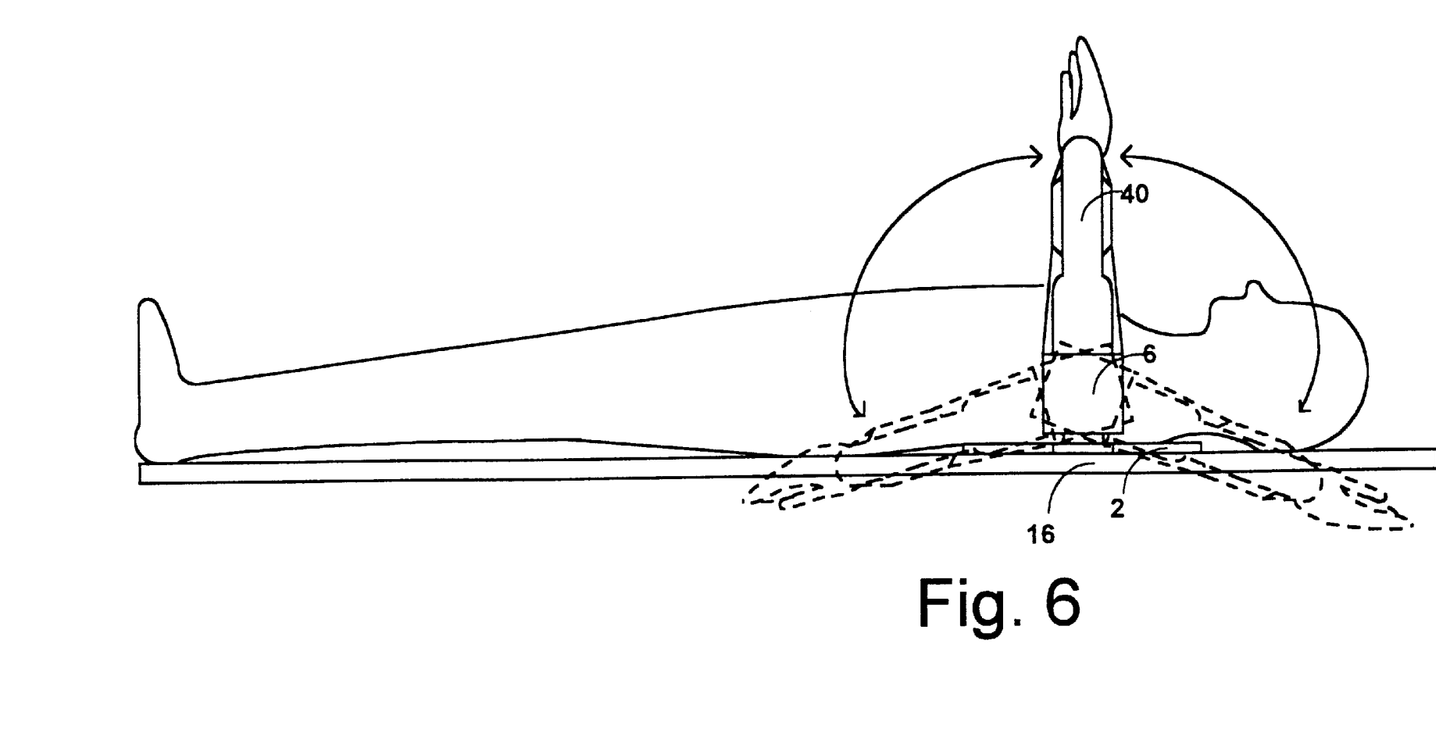
FIG. 6—is a side view of the invention applied to the left arm of a patient and illustrates rotation of the humerus about the central axis.

Referring to FIG. 5, the angle of abduction of the humerus in the frontal plane depicted as angle C is determined from signals from rotational angle sensors 38 and 66. The signal from rotational angle sensor 38 is indicative of angle A as indicated in FIG. 5. The signal from rotational angle sensor 66 is indicative of angle B. Angles A and B are utilized to calculate the angle of abduction of the humerus in the frontal plane, angle C, as shown in FIG. 5. As illustrated in FIG. 6, the signal from rotational angle sensor 56 is utilized to determine angle of rotation of elbow support 40 about bearing shaft 54 which is indicative of the angle of rotation of the humerus about its long axis relative to the back support 2. As can be seen from FIG. 1 and FIG. 2 the invention can be applied to either the left or right arm for testing. The apparatus allows the rotation of the humerus about the central axis to be varied between 120 degrees of internal rotation and 120 degrees of external rotation. The apparatus also allows the abduction of the humerus in the frontal plane to be varied from 0 degrees to 180 degrees. In practice this range is limited by the physiology of the test subject. The angle of abduction of the humerus in frontal plane and the angle of rotation about the central axis of the humerus relative to the back support 2 as calculated by the orientation calculator 76 are communicated to processor 78.

As shown in FIG. 4, the torque signal from torque sensor 58 indicative of the rotational torque applied about central axis of bearing shaft 54 is communicated to signal conditioner 80. Signal conditioner 80 acts to amplify the signal from torque sensor 58, and includes a low pass filter to remove unwanted noise from the signal. The amplified and filtered torque signal is then communicated to processor 78. Signals from single axis force sensors 30 are passed through filter 82 to remove noise and transient effects due to patient movement. The filtered signals are then communicated to back support force calculator 84 which calculates the sum of the forces measured by single axis force sensors 30 to provide a measure of total downward force on top plate 26 of back support 2. Back support force calculator 84 thereby produces a signal indicative of total downward force on top plate 26 of back support 2 which is communicated to processor 78.

Activity of a muscle in the body results in the presence of small electrical signals on the surface of the skin overlying the muscle. The magnitude and frequency spectrum of these electrical signals is related to the level of activity of the muscle and the electrical signals can be determined by placing electrode pairs on the skin surface over the muscle and measuring the differential voltage signal between the two electrodes.

As shown in FIG. 4, the electrical signal from electrode pair 8 applied to the patient 18 and the electrical signal from electrode pair 10 applied to patient 18 are communicated to amplifier 86. Single electrode 72 is utilized by amplifier 86 as ground reference to improve the rejection of unwanted electrical noise. Amplified signals from electrode pairs 8 and 10 are filtered by a 20 Hz–200 Hz band pass filter 88 to remove spurious signals and noise resulting from motion artifact or sources other than the activity of muscles underlying electrode pair 8 and electrode pair 10. The amplified and filtered signals from electrode pair 8 and electrode pair 10 representative of the activity of the muscles underlying electrode pair 8 and electrode pair 10 are communicated to processor 78. As described above, processor 78 receives as inputs signals indicative of: total downward force on top plate 26 of back support 2; the angle of abduction of the humerus in frontal plane and the angle of rotation about the central axis of the humerus relative to the back support 2; the rotational torque applied about the central axis of bearing shaft 54 through handle 44; and the activity of the muscles underlying electrode pair 8 and electrode pair 10.

User controls 90 allow an operator to control operation of processor 78 during use and display 92 provides visual feedback to the operator.

Processor 78 functions to control operation of the invention and to calculate and display the level of patient apprehension as a function of the orientation of the shoulder and forces applied to the humerus. Processor 78 functions as follows.

Processor 78 operates to determine reference levels and set threshold limits for testing by completing a calibration sequence. During the calibration sequence, the processor 78 firstly records the signal from back support force calculator 84 indicative of total downward force on top plate 26 of back support 2 when no external forces are applied to patient 18. This is the "back support force reference level". Processor 78 then calculates reference levels for muscle activity as a function of the magnitude and rate of change of magnitude of the electrical signals from electrode pair 8 and electrode pair 10. To obtain reference levels of muscle activity indicative of a minimum level processor 78 prompts the operator via display 92 to instruct the patient to relax their musculature for a predetermined time period during which processor 78 obtains and stores "resting" reference signals from electrode pair 8 and electrode pair 10 via filter 88. Next to obtain reference levels of muscle activity indicative of a maximum level processor 78 prompts the operator via display 92 to instruct patient 18 to contract their musculature to resist a predetermined rotational force applied to the humerus by the operator through handle 44 and measured by torque sensor 58 at a predetermined orientation of 30 degrees of internal rotation as indicated by the signal from orientation calculator 76 for a predetermined time period to obtain "voluntary contraction" reference signals via filter 88.

Reference levels acquired during the calibration phase are stored by processor 78 for later comparison to signals acquired during the testing sequence as described below and for comparison to the reference levels acquired during testing of the contralateral shoulder.

When processor 78 has completed the calibration sequence for the shoulder being assessed, processor 78 commences a testing sequence. During the testing sequence processor 78 operates as described below.

Processor 78 first prompts the operator via display 92 to manipulate the arm through a predetermined range of motion to perform the Apprehension Test. The operator is prompted to initially position the arm such that the angle of abduction in the frontal plane is 90 degrees and the humerus is at 45 degrees of internal rotation. Next the operator is prompted to manipulate the arm from the initial position to a position at which the humerus is at the maximum external rotation as permitted by the patient while maintaining the angle of abduction in the frontal plane 90 degrees. Processor 78 calculates the rate of change of the rotation of the humerus about its central axis by comparing the signal indicative of the orientation of the humerus as calculated by orientation calculator 76 to a signal from a clock contained within processor 78. During the manipulation of the arm, processor 78 provides feedback to the operator through display 92 by indicating level of applied rotational force measured by torque sensor 58 relative to predetermined reference thresholds and by indicating the rate of rotation of humerus about its central axis relative to predetermined thresholds, prompting the user to repeat the test if the rate of rotation and level of rotational force fall outside these thresholds.

During the manipulation of the arm, processor 78: (a) compares the levels of muscle activity as indicated by the signals from electrode pair 8 and electrode pair 10 via filter 88 to the previously determined "resting" and "voluntary contraction" reference levels of muscle activity;(b) provides an alarm to the user if the measured levels of muscle activity exceed the "voluntary contraction" reference levels; and (c) calculates and stores in memory the ratios of the levels of the signals from the electrode pair 8 and electrode pair 10 to the corresponding "voluntary contraction" reference levels obtained during the calibration process. The sum of the ratios for each electrode pair is indicative of the level of "Apprehension" as defined above.

It should be noted that a weighted sum of the ratios of the signals from electrode pair 8 and electrode pair 10 can be used effectively. If needed, additional electrode pairs may be used to form a weighted sum. Furthermore, the weighted sum may be compared to threshold levels and used as a warning to the operator or as a level to compare with previously measured levels.

Processor 78 continues the testing sequence by prompting the user via display 92 to perform the Relocation Test by applying a posteriorly directed force to the head of the humerus while maintaining the arm at the position of maximum external rotation as described above. During the Relocation Test processor 78: (a) calculates the level of force applied to the torso of the patient from the mathematical difference between output from back support force calculator 84 and the previously stored "back support force reference level" and calculates the time period during which force is applied; (b) provides an alarm to the operator if the calculated level of force does not meet or exceeds predetermined thresholds or if the time period during which the force is applied falls outside predetermined threshold limits; (c) compares the levels of muscle activity as indicated by the signals from electrode pair 8 and electrode pair 10 via filter 88 to the previously determined "resting" and "voluntary contraction" reference levels of muscle activity; (d) provides an alarm to the user if the measured levels of muscle activity exceed the "voluntary contraction" reference levels; and (e) calculates and stores in memory the ratios of the levels of the signals from the electrode pair 8 and electrode pair 10 to the corresponding "voluntary contraction" reference levels obtained during the calibration process. The sum of the ratios for each electrode pair is indicative of the level of "Apprehension" as defined above.

Processor 78 continues the testing sequence by prompting the user via display 92 to perform the Enhanced Apprehension Test by applying an anteriorly directed force to the head of the humerus while maintaining the arm at the position of maximum external rotation as described above. During the Enhanced Apprehension Test processor 78: (a) calculates the level of force applied to the torso of the patient from the mathematical difference between output from back support force calculator 84 and the previously stored "back support force reference level" and calculates the time period during which force is applied; (b) provides an alarm to the operator if the calculated level of force does not meet or exceeds predetermined thresholds or if the time period during which the force is applied falls outside predetermined threshold limits; (c) compares the levels of muscle activity as indicated by the signals from electrode pair 8 and electrode pair 10 via filter 88 to the previously determined "resting" and "voluntary contraction" reference levels of muscle activity; (d) provides an alarm to the user if the measured levels of muscle activity exceed the "voluntary contraction" reference levels; and (e) calculates and stores in memory the ratios of the levels of the signals from electrode pair 8 and electrode pair 10 to the corresponding "voluntary contraction" reference levels obtained during the calibration process. The sum of the ratios for each electrode pair is indicative of the level of "Apprehension" as defined above.

Processor 78 includes a clock for determining and recording the time at which the signals from electrode pair 8 and electrode pair 10 are produced and the corresponding orientation of the humerus, and includes memory means to store the results of testing from each shoulder on a single patient to allow comparison of the results from each shoulder by the operator.

When the calibration and testing sequences have been completed for both arm's of patient 18, processor 78 generates and communicates to printer 14 two reports. Examples of reports produced by the invention are shown in FIG. 7a and FIG. 7b and FIG. 8.

Figure 7A:
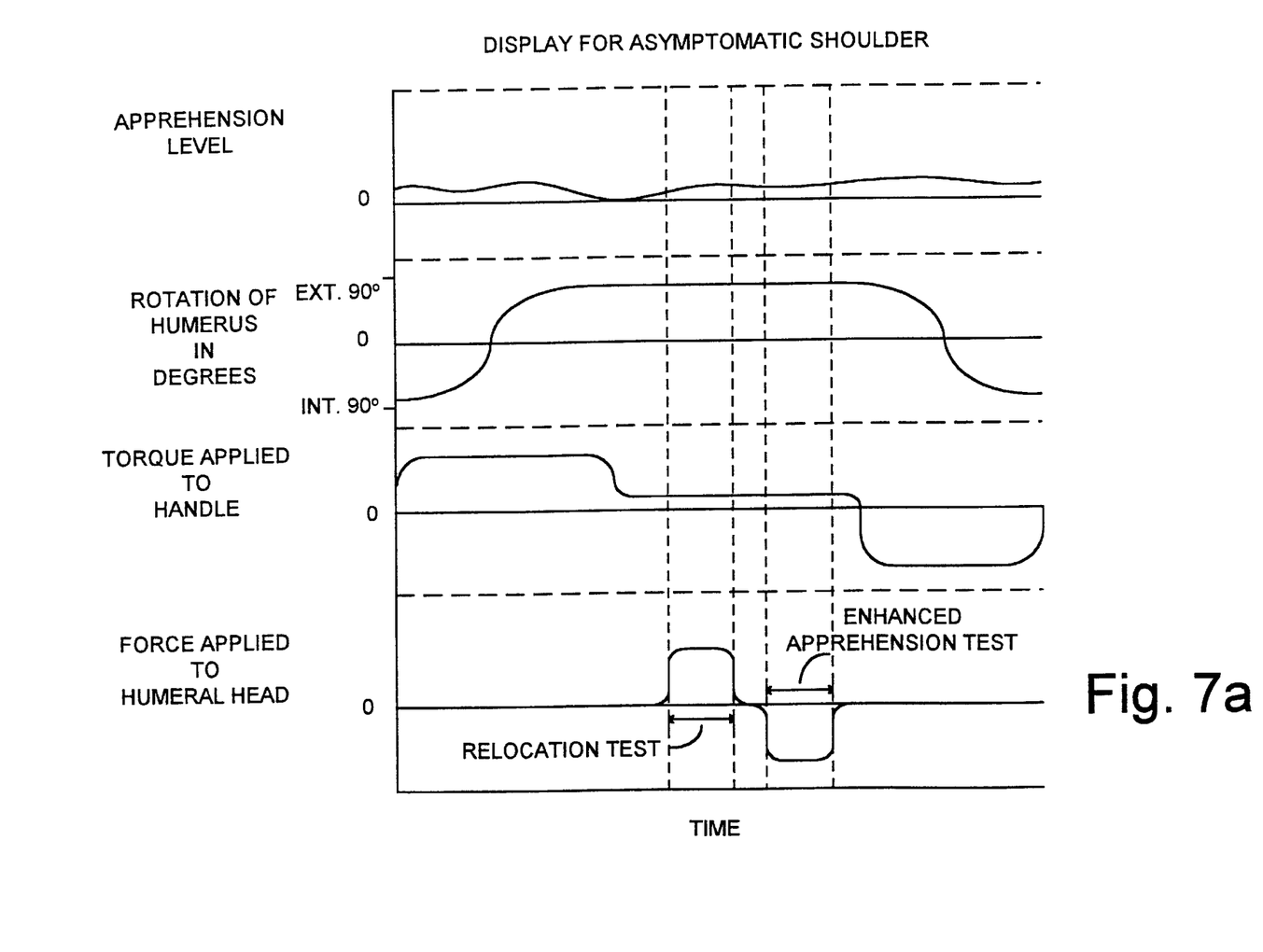
FIGS. 7a, 7b—illustrate a format for presenting the test results as a function of time.
Figure 7B:
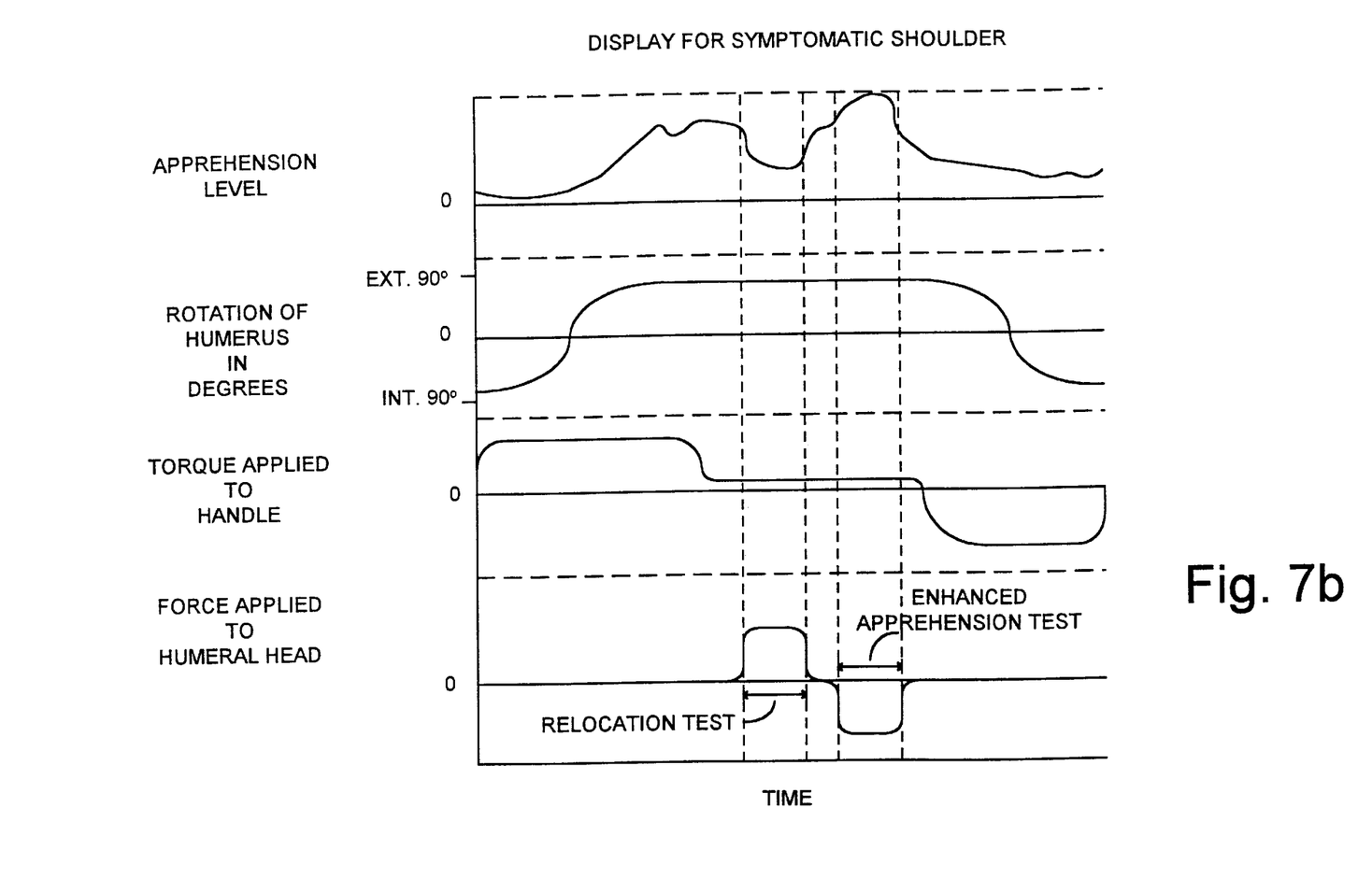

As shown in FIG. 7a and FIG. 7b the printed report is in the form of a graphical display indicating the calculated level of apprehension, the forces applied to the shoulder and the associated angle of humeral rotation as a function of time for each shoulder during Apprehension, Relocation and Enhanced Apprehension Testing. FIG. 7a depicts the results from testing on the asymptomatic shoulder of the patient, indicating that the level of apprehension remains relatively low as the humerus is externally rotated and the level of apprehension does not increase or decrease significantly during the application of force to the head of the humerus for Relocation and Enhanced Apprehension Testing. FIG. 7b depicts the results from testing on the symptomatic shoulder of the patient indicating: the level of apprehension increases significantly as the humerus is externally rotated; the level of apprehension decreases upon application of posteriorly directed force during Relocation Testing; and the apprehension level reaches a maximum during application of anteriorly directed force to the head of the humerus during Enhanced Apprehension Testing. The measured abduction angle calculated as shown in FIG. 4 and as described above is also indicated on the display for each shoulder.

Figure 8:
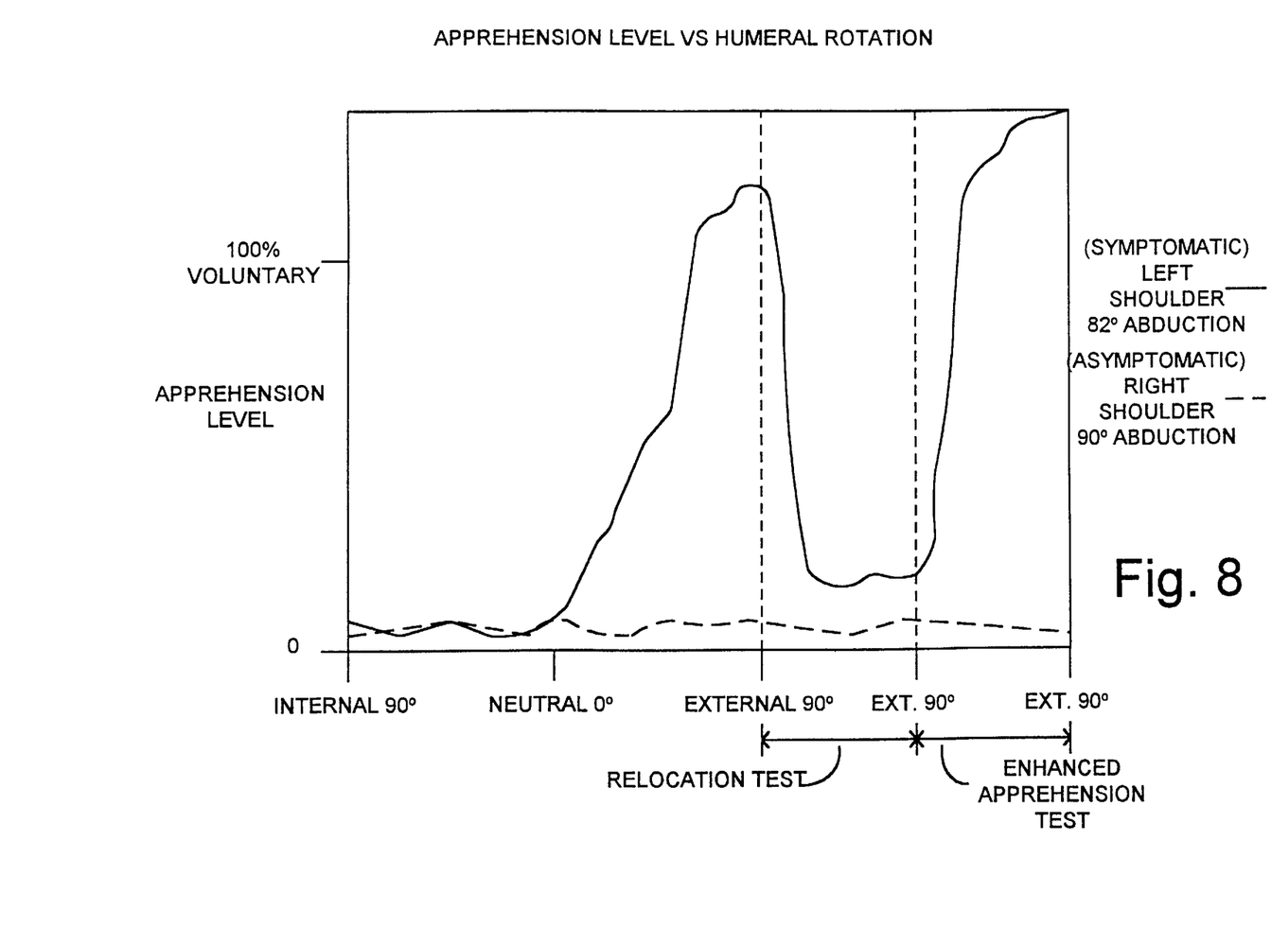
FIG. 8—illustrates a format for presenting test results as a function of the angle of rotation of the humerus about the central axis.

As shown in FIG. 8 the second printed report is in the form of a graphical display wherein the measured level of apprehension is plotted against humeral rotation, during Apprehension, Relocation and Enhanced Apprehension Testing for both shoulders. The measured abduction angle calculated as shown in FIG. 4 and as described above is also indicated on the display for each shoulder. As shown in FIG. 8, the apprehension level for the asymptomatic shoulder remains relatively low and relatively constant during testing. The apprehension level for the symptomatic shoulder increases significantly as the humerus is externally rotated, decreases significantly during Relocation Testing and reaches a maximum value during Enhanced Apprehension Testing.

Method of Use

The method of use of the invention is as follows: To assess the shoulder of a patient, patient 18 is first placed in a prone position on back support 2. The gridlines on top plate 26 are used as a guide to position the patient in a known orientation relative to back support 2. The arm associated with the shoulder being assessed is placed in elbow support 40 and secured using restraining straps 48 and 50. The patient's arm is abducted to the desired angle in the frontal plane. Electrode pairs 8 and 10 and the single electrode 72 are applied to the skin surface of patient over the muscles of the shoulder being assessed or elsewhere, such as on the face or on the muscles of the contralateral shoulder as required.

Muscle activity reference signals are obtained as described above. The operator then performs an Apprehension Test by rotating the humerus at a predetermined rate from an orientation of 45 degrees of internal rotation to the maximum external orientation as permitted by the patient. The operator then proceeds to perform a Relocation Test by applying a posteriorly directed force to the anterior head of the humerus using the hand. The operator then proceeds to perform an Enhanced Apprehension Test by applying an anteriorly directed force to the posterior head of the humerus using the hand.

The patient is then removed from the apparatus and the position of back support 2 is reversed to enable testing of the opposite shoulder of the patient. The opposite arm is placed in elbow support 40 and electrode pairs 8 and 10 are placed over the opposite shoulder or elsewhere as required, and the above procedure is repeated.

It is expected that during testing, the patient will remain relaxed and allow the humerus to be manipulated in the described manner without attempting to assist or resist. Occasionally it may be found that a patient will voluntarily assist or resist rotation of the humerus during test procedures. In these cases it is advantageous to apply electrode pairs 8 and 10 to measure the activity of a muscle that does not assist or resist rotation of the humerus about the central axis.

When the testing procedure is completed, two printed reports as described above are produced. An operator of the invention may use the reports to assess the stability of a shoulder by comparing the measured apprehension levels for the Apprehension Test, the Relocation Test and the Enhanced Apprehension Test for the symptomatic shoulder to those for the normal shoulder or those recorded from normal subjects.

Although this particular embodiment has been described, this was for the purpose of illustrating, but not limiting the invention. Various modifications which will come readily to one skilled in the art, are within the scope of the invention as defined in the appended claims.

We claim:

1. Apparatus for improved assessment of the function of a shoulder joint of a human subject, comprising:

humerus rotational angle transducing means for allowing rotation of the humerus of a subject around the long axis of the humerus in response to an applied rotational force and for producing an indication of the rotational angle of the long axis of the humerus relative to a reference;

physiological transducing means for producing an indication of the level of activity of a muscle of the subject;

muscle activity indication means for producing an indication of a first level of muscle activity at a first rotational angle and for producing an indication of a second level of muscle activity at a second rotational angle; and time indication means for producing an indication of the period of time during which the humerus rotates from the first rotational angle to the second rotational angle in response to the applied rotational force and for comparing the period of time to a reference time period and producing an indication of the period relative to the reference time period.

2. Apparatus as described in claim 1 and including computing means for determining the rate of rotation of the humerus and for determining the level of rotational force applied throughout the period to rotate the humerus around the long axis from the first rotational angle to the second rotational angle.

3. Apparatus as described in claim 2 and including rotational force application means operatively associated with the computing means and operable for applying the level of rotational force to the humerus throughout the time period.

4. Apparatus as described in claim 2 including a display means for displaying over time the rotational force determined by the computing means thereby to enable operation of the rotational force application means for applying a constant level of force throughout the period.

* * * * *